United States Patent [19]

Hoefle

[11] 4,285,951

[45] Aug. 25, 1981

[54] 2,2-DIMETHYL-5-(2,5-DIMETHYLPHENOXY)PENTYL ESTER OF 3-PYRIDINE CARBOXYLIC ACID AND USE AS AN ANTI-ATHEROSCLEROTIC AGENT

[75] Inventor: Milton L. Hoefle, Ann Arbor, Mich.

[73] Assignee: Warner-Lambert Company, Morris Plains, N.J.

[21] Appl. No.: 73,334

[22] Filed: Sep. 7, 1979

[51] Int. Cl.³ .................... A61K 31/44; C07D 213/55
[52] U.S. Cl. ...................................... 424/263; 546/342
[58] Field of Search ........................ 546/342; 424/263

[56] References Cited

U.S. PATENT DOCUMENTS

| 3,369,025 | 2/1968 | Bolhofer | 546/342 |
|---|---|---|---|
| 3,674,836 | 7/1972 | Creger | 560/61 |
| 4,115,393 | 9/1978 | Thiele et al. | 546/342 |

OTHER PUBLICATIONS

Noller, "Organic Chemistry", W. B. Saunders Company, Philadelphia, 1958, p. 128.

*Primary Examiner*—Henry R. Jiles
*Assistant Examiner*—Robert C. Whittenbaugh
*Attorney, Agent, or Firm*—Stephen I. Miller

[57] ABSTRACT

Certain pyridine derivatives of 1,1-dimethyl-4-(2,5-dimethylphenoxy)butane and their pharmaceutically-acceptable acid-addition salts are disclosed. These compounds increase the high density lipoprotein fraction of cholesterol found in the blood plasma.

3 Claims, No Drawings

2,2-DIMETHYL-5-(2,5-DIMETHYLPHENOXY)-PENTYL ESTER OF 3-PYRIDINE CARBOXYLIC ACID AND USE AS AN ANTI-ATHEROSCLEROTIC AGENT

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-atherosclerotic agents. The prior art contains many materials which are characterized as potentially useful anti-atherosclerotic agents. The prior art agents and intermediates for the same which applicant believes are most closely structurally related to the compounds of the present invention are as follows:

U.S. Pat. No. 3,369,025 discloses 3-pyridylmethyl(-substituted)phenoxy alkanoates which include 5-tolyloxy-5,5-dimethylpentanoic acid, 3-pyridinyl methyl ester;

U.S. Pat. No. 3,622,587 discloses intermediates of the structure:

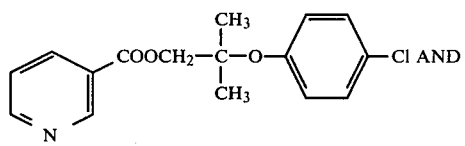

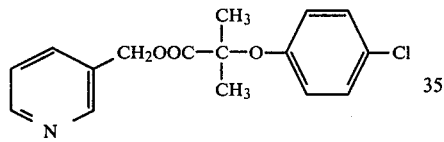

U.S. Pat. No. 3,674,836 claims 2,2-dimethyl-5-(2,5-xylyloxy)valeric acid.

The compounds of the present invention are useful as hypocholesterolemic agents and possess the additional advantage of elevating the high density lipoprotein fraction of cholesterol (HDL-cholesterol), which is known to lower the risk factor of coronary heart disease (Gordon, T. et al., High Density Lipoprotein as a Protective Factor Against Coronary Heart Disease, May 1977, The American Journal of Medicine, Vol. 62, pp. 707–714).

SUMMARY OF THE INVENTION

The invention relates to a compound of the formula:

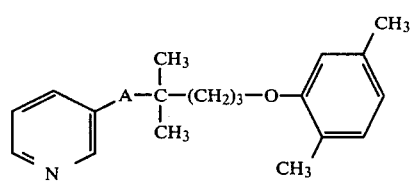

wherein A is

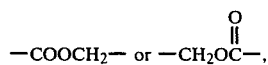

and the pharmaceutically-acceptable acid-addition salts thereof.

The invention also relates to processes for preparing the above-described compounds.

The invention also relates to the method of using the above-described compounds as anti-atherosclerotic agents for treating mammals.

The invention also relates to a pharmaceutical composition comprising a plasma high density lipoprotein increasing amount of a compound as described above as well as the pharmaceutically-acceptable acid-addition salts thereof and mixtures thereof.

DESCRIPTION OF THE PREFERRED EMBODIMENTS

The compounds of the invention wherein A is

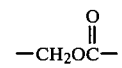

are prepared by reacting a compound of the formula I:

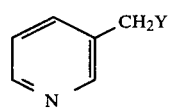

with a compound of the formula II:

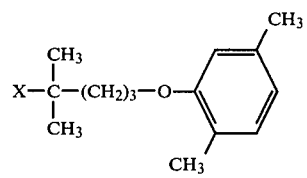

wherein Y is a hydroxyl group or a functionally equivalent reactive derivative thereof, and X is a carboxyl group or a functionally equivalent reactive derivative thereof. The term, functionally equivalent reactive derivative indicates a derivative of the specified function which when reacted with the other specified function (or its functionally equivalent reactive derivative) will produce the ultimately desired function, here an ester. Thus, when Y is hydroxyl, X in addition to carboxyl may be, for example, the acid halide such as the bromide or chloride, or a homo or hetero anhydride. When Y is, for example, a halide such as bromine or chlorine X may be a metal carboxylate such as the sodium, potassium, calcium or silver carboxylate. Other combinations of X and Y suitable for preparing the above-described compound will be familiar to those skilled in the art. Agents such as dicyclohexylcarbodiimide may also be utilized for direct ester formation when Y is hydroxyl and X is carboxyl. The preferred method for preparing the compound of the invention wherein A is

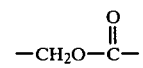

is to react the acid chloride of formula II with the alcohol of formula I. The reaction is carried out in a reaction-inert anhydrous solvent such as a halocarbon, a hydrocarbon or an ether. Examples of such solvents are chloroform, pentane, cyclohexane, benzene, furan, diethyl ether, and the like. The reaction is preferably carried out at room temperature or below, most preferably at a temperature of from 0° to 10° C. The reaction time is not particularly critical. The reaction is usually complete within two to twenty hours. During the last stages of the reaction it is preferable to boil the reaction mixture for a time to ensure completeness of the reaction. The product can be isolated and purified in the conventional manner, e.g., washing with dilute base to remove the acid generated by the reaction followed by vacuum distillation of the organic layer. If desired, the reaction can be carried out in the presence of an acid scavenger such as potassium carbonate, sodium bicarbonate, an organic tertiary amine, and the like. The starting acid chloride may be prepared from the corresponding acid (described in U.S. Pat. No. 3,674,836) by methods familiar to those skilled in the art, for example treatment with thionyl chloride or oxalyl chloride.

The compounds of the invention wherein A is —COOCH$_2$— are prepared by reacting a compound of the formula III:

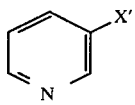

with a compound of the formula IV:

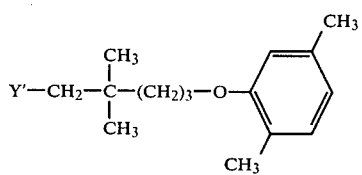

wherein X' is a carboxyl group or a functionally equivalent reactive derivative thereof and Y' is a hydroxyl group or a functionally equivalent reactive derivative thereof. The contemplated functionally equivalent reactive derivatives of X' and Y' are the same as those defined and exemplified, hereinabove respectively for X and Y. The preferred method for preparing the compound of the invention wherein A is —COOCH$_2$— is by the reaction of the acid chloride of formula III with the alcohol of formula IV. The procedure for carrying out this reaction is substantially identical to that described hereinabove for the reaction of compound I wherein Y is hydroxyl with compound II wherein X is the acid chloride. The starting alcohol of formula IV may be prepared, for example, by the reduction of the corresponding acid with lithium aluminum hydride as described in U.S. Pat. No. 3,707,566.

The pharmaceutically-acceptable acid-addition salts of the invention can be prepared by reacting the free base with a suitable inorganic or organic acid in the conventional manner. Suitable acids, for purposes of the invention, are those which form pharmaceutically-acceptable acid-addition salts such as; hydrochloric, sulfuric, phosphoric, acetic, fumaric, citric, benzoic, substituted and unsubstituted sulfonic acids and the like.

The compounds of the invention can exist in unsolvated as well as solvated forms, including hydrated forms. In general, these solvated forms with pharmaceutically-acceptable solvents such as water, ethanol and the like are equivalent to the unsolvated forms for purposes of the invention.

The free base compounds of the invention and their salts differ somewhat in certain physical properties, such as solubility in polar solvents, but they are otherwise equivalent for purposes of the invention.

The compounds of the invention are new chemical substances, of value as pharmacological agents which reduce serum cholesterol levels. An important property of these compounds is that they not only reduce total cholesterol levels but they increase the high density lipoprotein fraction of cholesterol (HDL-cholesterol) at the expense of the low density lipoprotein fraction of cholesterol. The risk of coronary heart disease is thereby reduced. The assay by which this utility was established is carried out as follows.

Treatment of Animals

The experiments were based on the screening procedure described by Schurr et al., "High Volume Screening Procedures for Hypobetalipoproteinemic Activity in Rats." In: Atherosclerosis Drug Discovery, Ed. C. E. Day, Plenum Press, New York, p. 215–229, 1976. Male Charles River CDF rats, initial weight 80–100 grams, were fed for 7 days a diet containing ground Purina Laboratory Chow No. 5010, 5.5% added peanut oil, 1.5% cholesterol, and 0.5 cholic acid. On days 4 through 7, test compounds were dosed by oral gavage; control rats received vehicle only. The dosing vehicle was 4% acacia at a volume of 0.25 ml per 100 gm body weight. Groups of 10 rats were used for each compound. After overnight fast, on day 8 the rats were etherized and blood was taken from the heart atrium into Vacutainer tubes containing 0.048 ml of 15% EDTA to give a final concentration of 0.14% EDTA. Plasma was obtained by centrifugation at 5° C. for 15 minutes at 1200 x g.

Analytical.

Total cholesterol and triglyceride levels were determined in aliquots of the plasmas by standard Auto Analyzer II methodology (Method AAII-24). Other 1 ml aliquots were treated with 50 μl of 1 M MnCl$_2$+40 μl of 5000 units/ml heparin, Bruistein et al., "Rapid Method for the Isolation of Lipoproteins by Electrophoresis on Polyacrylamide Gel.," Clin. Chem. 23: 1826–1833 (1970), centrifuged, and cholesterol was determined in the supernatants by AutoAnalyzer II. Further aliquots were electrophoresed in polyacrylamide gels using the Ames RediDisc Kit, Lopes-Virella et al., "Cholesterol Determination in High-Density Lipoproteins Separated by Three Different Methods," Clin. Chem 23: 882–884 (1977), and ratios of alpha-migrating to beta-migrating lipoprotein concentrations were measured with a Helena Laboratories Auto Scanner densitometer. For analysis of liver cholesterol and triglycerides, 0.5 g portions of liver were homogenized with 9.5 ml of 2-propanol in a Polytron homogenizer followed by 15 minutes of shaking in a mechanical shaker. Aliquots of 0.125 ml of the homogenate were processed by the AutoAnalyzer II methodology. The significance of differences between treated groups and control groups was evaluated by the student t test.

A compound is considered active in this procedure if it increases the HDL fraction of cholesterol by at least 50%. The test results obtained for the compounds of the invention as well as for 2,2-dimethyl-5-(2,5-xylyloxy)-valeric acid (U.S. Pat. No. 3,674,836) are shown in the following table.

TEST RESULTS

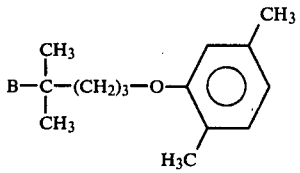

| B | Dose mg/kg | Percent Change | | | | Percent Wt. Gain Inhibition | Liver Wt. Percent Change |
| --- | --- | --- | --- | --- | --- | --- | --- |
| | | Plasma Cholesterol | Plasma TG | HDL Cholesterol | HDL/LDL Electrophoretic | | |
| 3-pyridyl-CH₂O—C(=O)— | 50 | −49 | +63 | +212 | +179 | 0 | +26 |
| 3-pyridyl-C(=O)—OCH₂— compound tested as hydrochloride | 50 | −23 | +26 | +243 | +399 | 0 | +11 |
| HOC(=O)— compound of U.S. Pat. No. 3674836 | 50 | −42 | +28 | +166 | +138 | 0 | +13 |

The compounds of the invention can be administered either orally or parenterally. They can be combined with a solid or liquid carrier or diluent and made available in varying amounts in such pharmaceutical forms as tablets, capsules, powders, and aqueous and non-aqueous suspensions and solutions.

The invention is illustrated by the following examples.

EXAMPLE 1

A solution of 9.4 g of 2,2-dimethyl-5-(2,5-dimethylphenoxy)pentanol in 50 ml of methylene chloride is added dropwise to an ice-cold solution of 7.12 g of nicotinyl chloride hydrochloride in 150 ml of methylene chloride containing 8.08 g of triethylamine. The mixture is heated for two hours. Upon cooling, the mixture is washed with water, dried over anhydrous magnesium sulfate and evaporated to dryness to give the 2,2-dimethyl-5-(2,5-dimethylphenoxy)pentyl ester of 3-pyridine carboxylic acid as an oil. The crude 2,2-dimethyl-5-(2,5-dimethylphenoxy)pentyl ester of 3-pyridine carboxylic acid is converted to its hydrochloride salt by treatment with hydrogen chloride to yield the desired 2,2-dimethyl-5-(2,5-dimethylphenoxy)pentyl ester of 3-pyridine carboxylic acid, monohydrochloride, m.p. 129°–130° C. following crystallization from isopropanol; yield 5 g.

EXAMPLE 2

The acid chloride obtained from 12.5 g of 2,2-dimethyl-5-(2,5-dimethyphenoxy)pentanoic acid is dissolved in 60 ml of benzene and added dropwise to an ice-cold solution of 10.9 g of pyridine-3-carbinol in 60 ml of benzene. The mixture is stirred at room temperature overnight followed by refluxing for two hours. The benzene solution is washed with water, dried over anhydrous magnesium sulfate and evaporated to dryness. The residual oil is distilled in vacuo to yield the desired 5-(2,5-dimethylphenoxy)-2,2-dimethylpentanoic acid, 3-pyridinyl methyl ester, b.p. 190° C. at 0.06 mm of Hg; yield 12 g.

The 2,2-dimethyl-5-(2,5-dimethylphenoxy)valeric acid chloride may be prepared by dropwise addition of 34 ml of oxalyl chloride in 75 ml of benzene to an ice-cold solution of 12.5 g of 2,2-dimethyl-5-(2,5-dimethylphenoxy)valeric acid in 75 ml of benzene, stirring the mixture at 0° C. for one hour and at room temperature for one and one-half hours, followed by removal of the benzene under reduced pressure at 40° C. or below.

I claim:

1. The compound which is the 2,2-dimethyl-5-(2,5-dimethylphenoxy)pentyl ester of 3-pyridine carboxylic acid, and the pharmaceutically-acceptable acid-addition salts thereof.

2. A pharmaceutical composition comprising a plasma high density lipoprotein chloresterol fraction increasing amount of a compound as defined in claim 1, and the pharmaceutically-acceptable acid-addition salts thereof.

3. A method of treating a mammal suffering from atherosclerosis which comprises administering to said mammal an anti-atherosclerotic effective amount of a compound as defined in claim 1, and the pharmaceutically-acceptable acid-addition salts thereof.

* * * * *